(12) United States Patent
Heiberger et al.

(10) Patent No.: US 9,326,673 B2
(45) Date of Patent: May 3, 2016

(54) DIAGNOSTIC DEVICE FOR DETECTING A LAYER BOUNDARY IN AN EYE AND RING ELEMENT FOR THE DIAGNOSTIC DEVICE

(76) Inventors: Kurt Heiberger, Nuremberg (DE); Andreas Schnalke, Nuremberg (DE)

( * ) Notice: Subject to any disclaimer, the term of this patent is extended or adjusted under 35 U.S.C. 154(b) by 0 days.

(21) Appl. No.: 13/581,577

(22) PCT Filed: Mar. 4, 2011

(86) PCT No.: PCT/EP2011/053276
§ 371 (c)(1),
(2), (4) Date: Sep. 18, 2012

(87) PCT Pub. No.: WO2011/107584
PCT Pub. Date: Sep. 9, 2011

(65) Prior Publication Data
US 2013/0135585 A1 May 30, 2013

(30) Foreign Application Priority Data
Mar. 5, 2010 (DE) .......................... 10 2010 010 569

(51) Int. Cl.
*A61B 3/10* (2006.01)
*A61B 3/00* (2006.01)
*A61B 3/117* (2006.01)

(52) U.S. Cl.
CPC ............... *A61B 3/0008* (2013.01); *A61B 3/117* (2013.01)

(58) Field of Classification Search
CPC ........ A61B 3/0008; A61B 3/14; A61B 3/152; A61B 3/103; A61B 3/113; A61B 3/107; A61B 3/04; A61B 3/1225; A61B 3/1015; A61B 5/1455; A61B 5/14532; A61B 5/0059
USPC ......... 351/206, 208, 210, 211, 212, 221, 236, 351/246; 600/310, 316, 318, 319, 476
See application file for complete search history.

(56) References Cited

U.S. PATENT DOCUMENTS

| | | | |
|---|---|---|---|
| 5,459,570 A | 10/1995 | Swanson et al. | |
| 6,806,963 B1 | 10/2004 | Waelti et al. | |
| 2007/0078308 A1* | 4/2007 | Daly | ............................. 600/310 |
| 2007/0123761 A1* | 5/2007 | Daly et al. | .................... 600/316 |
| 2007/0123768 A1 | 5/2007 | Freedman | |

FOREIGN PATENT DOCUMENTS

| | | |
|---|---|---|
| DE | 197 15 212 A1 | 10/1997 |
| DE | 10 2006 005 473 A1 | 11/2006 |
| DE | 10 2007 017 611 A1 | 10/2008 |
| EP | 1 358 839 A1 | 11/2003 |

(Continued)

*Primary Examiner* — Thomas K Pham
*Assistant Examiner* — Jie Lei
(74) *Attorney, Agent, or Firm* — Lucas & Mercanti, LLP

(57) ABSTRACT

A diagnostic device detects a layer boundary which facilitates the determination of layer thicknesses in the human eye. The device has a light source with a beam path which is designed to guide at least one measuring beam of the light source from the object plane of the light source into an intersecting region of the measuring beam with an optical axis in the eye, and an actuator designed to move the intersecting region along the optical axis. The beam path guides the measuring beam from a layer boundary into the sensor unit. An evaluation unit is designed to estimate and/or determine a layer thickness between a first and a second layer boundary.

5 Claims, 11 Drawing Sheets

(56) References Cited

FOREIGN PATENT DOCUMENTS

| | | |
|---|---|---|
| EP | 1 785 690 A1 | 5/2007 |
| GB | 2 407 378 A | 4/2005 |
| GB | 2 409 033 A | 6/2005 |
| JP | 2003 052632 A | 2/2003 |
| JP | 2004 236843 A | 8/2004 |
| WO | 02/080760 A1 | 10/2002 |
| WO | 2004/034894 A1 | 4/2004 |

* cited by examiner

DIAGNOSTIC DEVICE FOR DETECTING A LAYER BOUNDARY IN AN EYE AND RING ELEMENT FOR THE DIAGNOSTIC DEVICE

CROSS-REFERENCE TO RELATED APPLICATIONS

This application is a 371 of PCT/EP2011/053276 filed Mar. 4, 2011, which in turn claims the priority of DE 10 2010 010 569.4 filed Mar. 5, 2010, the priority of both applications is hereby claimed and both applications are incorporated by reference herein.

BACKGROUND OF THE INVENTION

The invention relates to a diagnostic device for detecting a layer boundary in an eye, a lens or another translucent body, with a light source, wherein the light source defines an object plane, with a sensor unit, with a beam path which is designed to guide at least one measuring beam of the light source from the object plane of the light source into an image plane and/or into an intersecting region of the measuring beam with an optical axis in the eye, with an actuator designed to move the image plane and/or the intersecting region along the optical axis, wherein the beam path is designed such that, in a detection state, the measuring beam is guided from a layer boundary of the eye into the sensor unit if the image plane and/or the intersecting region is located on the layer boundary, and with an evaluation unit designed to recognize the detection state on the basis of the signals of the sensor unit. The invention also relates to a ring element for the diagnostic device.

For the treatment of the human eye, for example when performing cornea corrections using laser beams, precise information on the inner structure of the eye is required. In many areas of application, information about the eye is combined into a 3D eye model. The cornea of the eye, being the foremost layer of the eye, is of particular importance for modeling. The corneal thickness, for example, is of relevance for correcting the intraocular pressure as measured by tonometry, since the value of the intraocular pressure as measured by commonly used methods depends on the corneal thickness.

A pachymeter (sometimes also called a pachometer) is a measuring instrument for measuring the corneal thickness of the human eye. The pachymeters known in the art are based on different measurement techniques:

One implementation of a pachymeter on the basis of non-contact optical measurement involves a measurement technique called OLCR (optical low-coherence reflectometry). Another implementation which, however, requires contact is the determination of the corneal thickness using ultrasound, for which a small ultrasound probe is placed on the cornea. In principle, both implementations allow for the determination of corneal thickness, anterior chamber depth, intraocular lens thickness and eye length to a precision of a few micrometers. Another way of measuring the anterior part of the eye is to combine a slit lamp with a Scheimpflug camera. This measuring instrument assembles the 3D image of the eye from several individual measurements where the eye is measured in several layers and the Scheimpflug camera takes a picture of each sectional plane.

All three measurement techniques have their weaknesses due to their working principles. Ultrasound measuring instruments, for example, have the disadvantage that they need to be placed full-contact on the eye, a procedure only a skilled expert can carry out in a reproducible way. The system comprising a Scheimpflug camera and a slit lamp is comparatively large, which makes it difficult to integrate into a treatment laser, for example. The measuring instruments based on the OLCR technique can usually only measure distances within the visual axis of the eye.

The aim of the present invention is to propose a diagnostic device for detecting a layer boundary which facilitates the determination of layer thicknesses in the human eye. A further aim of the present invention is to present a special optical element for said diagnostic device.

A diagnostic device for detecting a layer boundary in an eye, a lens or another translucent body is proposed within the scope of the invention. In particular, one or several layer boundaries in the region between the cornea and the lens in the anterior part of the eye can be detected. Said anterior part of the eye contains the cornea, the anterior chamber and the lens. Some layer boundaries which are possible to detect are the following:

a) layer boundary: external side of the cornea
b) layer boundary: cornea—anterior chamber
c) layer boundary: anterior chamber—lens
d) layer boundary: lens—vitreous body.

The diagnostic device is preferably designed as a pachymeter which is used to measure the corneal thickness of the human eye, among other things. In alternative fields of use it is also possible to measure other translucent bodies, e.g. lenses, in particular contact lenses.

The diagnostic device comprises a light source, said light source being preferably designed as a laser source or a light-emitting diode, in particular a superluminescent diode. The light source defines an object plane, wherein the object plane may be located at the position of the light source or at an intermediate image of the light source.

The light source facilitates the emission of at least one measuring beam, in particular a measuring laser beam, which can be bounced back, in particular reflected, from one or several layer boundaries in the eye. The wavelength of the light source is preferably in the visible spectrum, meaning e.g. between 400 nm and 650 nm.

As a further component, the diagnostic device comprises a sensor unit designed for detecting the at least one measuring beam.

A beam path serves to guide and optionally shape the at least one measuring beam from the object plane of the light source into an image plane and/or into an intersecting region of the measuring beam with an optical axis in the eye. The optical axis may correspond, for example, to a symmetry axis of the beam path but can also be selected arbitrarily. Through the beam path, the light source (or an image thereof) is projected into the image plane and/or the intersecting region, with the projection being a real image of the light source and/or a measuring point formed by the light source.

The diagnostic device has an actuator which is designed to move the image plane and/or the intersecting region along the optical axis. With the actuator, it is thus preferably possible to influence the beam path such that the focal position and/or the lateral position of the measuring beam in the eye is changed, which makes at least a movement of the image plane and/or the intersecting region along the optical axis possible.

Furthermore, the beam path is designed such, in a detection state, the measuring beam is guided from a layer boundary in or on the eye into the sensor unit if the image plane and/or the intersecting region is located on the layer boundary. The actuator thus serves to vary the condition of incidence of the measuring beam onto and/or into the eye until the detection state is reached, said detection state being a state where the measuring beam is guided from the layer boundary through the beam path into the sensor unit as a directed or diffuse reflection.

As a further component, the diagnostic device has an evaluation unit designed to recognize the detection state on the basis of the signals of the sensor unit.

To summarize, a detection state with regard to a layer boundary is detected if and only if the measuring beam is guided back into the sensor unit. The detection on the basis of the signals of the sensor unit can be performed, for example, by using the position of the returning measuring beam, the intensity of the returning laser beam etc.

Within the scope of the invention, it is proposed to estimate and/or determine a layer thickness between a first and a second layer boundary on the basis of the position of the actuator in a detection state of the first and the second layer boundary.

It is therefore an idea of the invention to operate the actuator such that the detection state of a first layer boundary is detected and the position of the actuator is recorded. In a further step, the detection state of a second layer boundary is detected and again the position of the actuator is recorded. Since the beam path is known, it is now possible to estimate and/or determine the distance between the two layer boundaries and hence the layer thickness between the layer boundaries. In this context, the term "estimate" relates to a procedure to be followed if not all required parameters of the beam path and/or the eye are sufficiently known and, for example, estimated parameters have to be used. If all parameters are sufficiently known, the layer thickness can be determined, in particular calculated precisely, using these parameters.

In a first possible embodiment of the invention, the beam path is designed such that an image of the light source can be projected into the image plane in the eye. In particular, the measuring beam is expanded within the beam path, which means that it is guided, at least in sections, with a beam diameter, in particular an outer beam diameter (FWHM), larger than 3 mm, preferably larger than 5 mm. The actuator is preferably designed as an adaptive optical element, such as an adaptive lens, in particular a fluid lens, and/or as a movable optical element, in particular a slidable optical element, such as a slidable lens. In particular, the beam path is designed such that the measuring beam on its way to the eye overlaps with itself on its way back to the sensor unit in the region between the eye and the first optical element. In this embodiment, the diagnostic device is designed similar to a confocal microscope, with the detection state being reached precisely when the image plane is located on the layer boundary and thus a confocal lighting condition exists.

In another embodiment of the invention, the measuring beam is propagated, at least in sections, in an unexpanded way, and in particular only a single measuring laser beam is employed. Between the light source and the eye, and in particular between the last optical element and the eye, said measuring beam, being unexpanded, has a diameter (FWHM) which is always smaller than 2 mm, in particular smaller than 1 mm. It is particularly preferred in this embodiment that the actuator is designed as a scanning means, in particular as a 2D scanning mirror. By way of the scanning means, the measuring beam can perform scanning of the eye in the depth direction along the optical axis and laterally e.g. linear scanning and/or scanning of the entire surface, thus reaching the detection state. In the detection state the individual measuring beam is preferably guided back to the sensor unit on a different beam path, in particular between the eye and the adjacent optical element.

What both embodiments have in common, however, is that the measuring beam can be guided back via the eye, in particular via the layer boundary, into the sensor unit and the evaluation unit can recognize the detection state on the basis of the signals of the sensor unit only in certain positions of the actuator.

To achieve sufficient measurement accuracy it is possible, for example, to arrange a spatial filter and/or an aperture in the beam path in front of the sensor unit, wherein said spatial filter and/or aperture ensures that the measuring beam can be guided back onto the sensor unit only in the detection state with sufficient measurement accuracy.

Another possibility is to design the sensor unit as a unit with spatial resolution, in which case the sensor unit may be designed, for example, as an image capture chip, such as a CMOS chip or a CCD chip, or as a position sensitive diode (PSD). In these embodiments, detection can be achieved by having the evaluation unit interpret the position and/or intensity of the returning measuring beam with regard to the detection state.

In a particularly advantageous embodiment of the invention, the beam path is designed such that the measuring beam for detecting the layer boundary is restricted to one ring area or a smaller area on at least one optical element, in particular the last optical element in front of the eye, thus leaving a central region, in particular an aperture region, uncovered. The reasoning for this arrangement is the observation that using an outer region is sufficient for detecting the layer boundary, so that the central region can be left uncovered for other measuring and/or control beams. In particular, it is possible to arrange an optical element in the central region that is different from the optical element in the ring area or the edge area.

Preferably, the ring area has an optical component, in particular designed as a ring element, which guides the measuring beam onto the image plane and/or onto the intersecting region and which is designed as a diffractive optical element and/or a diffractive element and/or a reflecting element. Particularly preferably, the optical component is implemented such that the intersecting region is moved along the optical axis by changing the radial position of the measuring beam passing through in relation to the optical axis.

In a further form of the invention, the optical component has several regions in the direction of rotation around an or the optical axis, said regions guiding the measuring beam into different regions, in particular depth regions, along the optical axis. This embodiment is based on the consideration that there is regularly a distance larger than 5 mm between the first possible layer boundary, which is located between the surrounding area and the cornea, and the last possible layer boundary, which is located between lens and vitreous body. To achieve a sufficiently high measurement accuracy, such as better than 20 micrometer, preferably better than 10 micrometer, the different regions are arranged in the direction of rotation, said regions guiding the measuring beam into different regions along the optical axis. A first region thus guides the measuring beam into the region of the cornea, another region guides the measuring beam, for example, into the region of the lens, etc.

In an advantageous further form of the invention, the beam path is designed such that accommodation beams can be sent through the central region of the ring area, said accommodation beams forming an accommodation target in the eye. For example, a regular lens is arranged in the central region, said lens guiding or shaping the accommodation beams. The accommodation target provides a stimulus to the eye to fixate in a certain position with a certain prestressing of the lens, so that reproducible measurements of the layer thicknesses can be carried out.

In a possible further form of the invention, several accommodation targets may be formed which appear to the eye to be coming from different directions. The patient can be instructed during the diagnosis to fixate on the respective current accommodation target so that the eye of the patient is turned into a defined position. In this new position it is again possible to measure the layer thicknesses of the cornea etc., making it possible for the diagnostic device to generate a two-dimensional network of values measured for the layer thicknesses, depending on the number of accommodation targets.

In an advantageous embodiment of the invention, the accommodation beams and the measuring beams are created by the same light source. The light source has a dual function in this case, with the beams guided through the ring area being interpreted and used as measuring beams and the beams guided through the central region serving as accommodation beams for creating the accommodation target.

A further object of the invention relates to a ring element for a diagnostic device as described above or according to any one of the preceding claims, wherein the ring element has several regions in the direction of rotation, with pairs of said regions being assigned to a layer boundary of the eye.

In the following, the advantages of the invention will be shown with reference to the embodiments:

The main function of the diagnostic device is the non-contact measurement of layer thicknesses in the human eye. It is advantageous that the layer thicknesses of the eye can be measured in a defined state of the eye due to the optionally integrated accommodation target, said accommodation target putting the eye in a defined and reproducible state. The accommodation target can make an eye test character wander in the x and y direction as desired, and thus the eye to be measured can follow the eye test character. This makes it possible to turn the eye in all directions in a defined manner. It can also be provided, for example, that an observation camera records the rotation angle of the eye and the position of the eye, so that layer thicknesses can be measured at different positions and thus covering the entire surface. Due to its possible small size, in particular, the diagnostic device can be integrated in or combined with a topography measuring instrument and/or a wavefront measuring instrument. In this embodiment, the eye can be fully measured with a single diagnostic device. A 3D model of the eye can be created using the values measured by the diagnostic device, and said 3D model can then be utilised, for example, for correcting the refractive power in refractive surgery. Again because of its possible small size, the diagnostic device can be integrated into a treatment laser used for correcting the refractive power of the eye. The diagnostic device can measure the layer thickness of the cornea in situ and in real-time and monitor and control the results of the laser treatment.

BRIEF DESCRIPTION OF THE DRAWINGS

Other features, advantages and effects of the present invention are derived from the following description of preferred embodiments of the invention and the accompanying figures. The figures show.

DETAILED DESCRIPTION OF THE PREFERRED EMBODIMENTS

Figure 1:
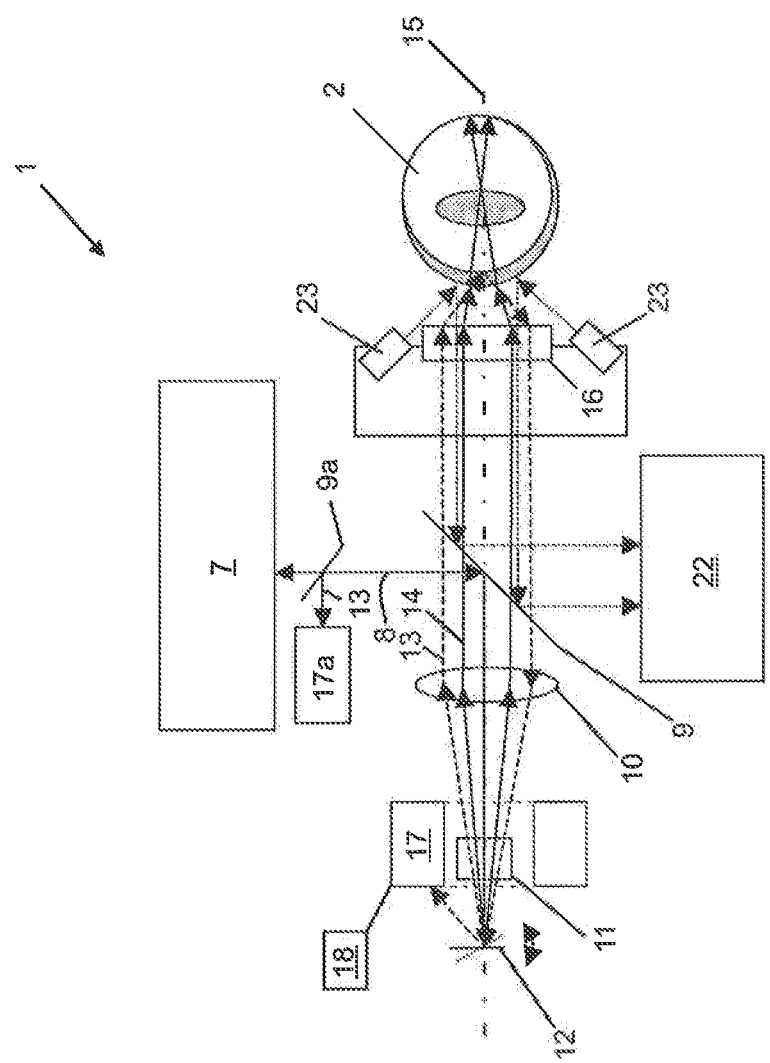
FIG. 1 a block diagram of a diagnostic device as a first embodiment of the invention.

FIG. 1 shows a very schematic view of a diagnostic device 1 as a first embodiment of the invention. The diagnostic device 1 has the purpose of measuring layer thicknesses in a human eye 2 and can be designed as a pachymeter.

Figure 11:
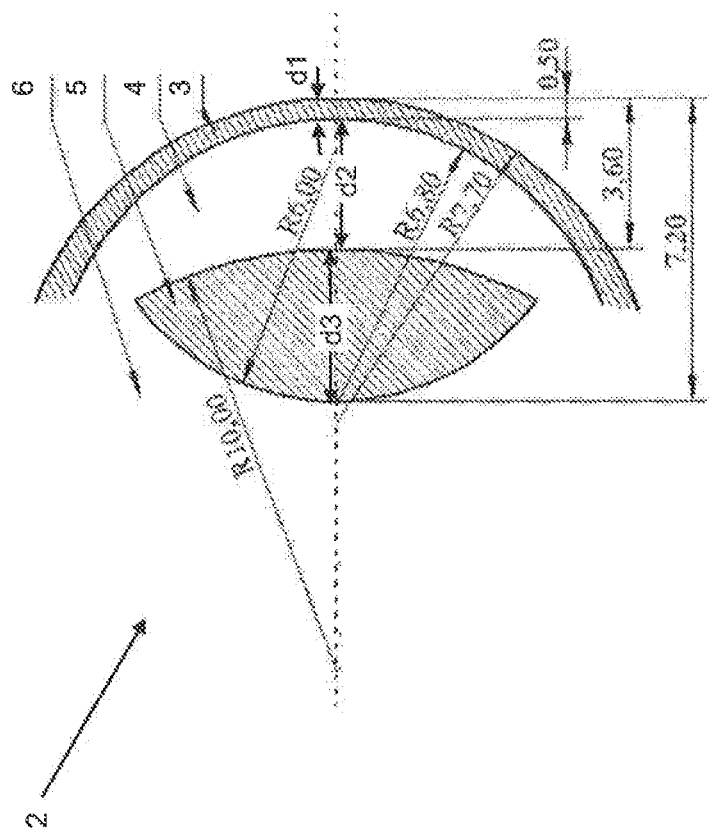
FIG. 11 a schematic cross-sectional view of a human eye to illustrate the regions in the eye.

The layer thicknesses to be measured are displayed in FIG. 11 which shows a cross-section of the anterior part of the eye 2. A first layer is formed by the cornea 3, followed by the anterior chamber 4 and the lens 5 in the eye 2. Behind the lens 5 extends the vitreous body 6. The diagnostic device 1 is used to measure, in particular, the layer thickness d1 between the external side of the cornea 3 and the adjacent anterior chamber 4. Another possible layer thickness d2 is the distance between the back side of the cornea 3 and the front side of the lens 5. A third possible layer thickness to be measured is the thickness d3 of the lens 5. The layer thickness d1 of the cornea 3 is in the magnitude of 0.5 mm, the thickness d2 of the anterior chamber 4 is in the magnitude of 3.6 mm and the thickness d3 of the lens 5 is in the magnitude of 3.6 mm, as well. It is also possible to record other layer thicknesses or combined layer thicknesses like the distance between the back side of the cornea 3 and the back side of the lens 5.

Coming back to FIG. 1, the beam path for detecting a layer boundary in the eye 2 will be described in the following. A laser beam 8 is emitted by a laser diode module 7 and guided onto a polarizing beam splitter 9 which deflects the laser beam 8 by 90 degrees and completely reflects it. The laser beam 8 then passes through a lens 10, subsequently through a quarter-lambda waveplate 11 and then hits a scanning micromirror 12. The scanning micromirror 12 facilitates two-dimensional tilting around mutually perpendicular pivot axes. The scanning micromirror 12 is preferably constructed as a resonant system which, depending on the excitation, performs the same tilting operations at regular intervals.

The laser beam 8 of the laser diode module 7, which is guided via the scanning micromirror 12, will be used both as a measuring laser beam 13 and as an accommodation laser beam 14 in the following. The measuring laser beams 13 are drawn as dotted lines in FIG. 1 and will be described in the following. Starting from the scanning micromirror 12, the measuring laser beam 13 passes through the quarter-lambda waveplate 11 and is shaped by the lens 10 parallel to an optical axis 15 of the diagnostic device 1. Because of the phase rotation, the measuring laser beam 13 then passes through the beam splitter 9 without any deflection in relation to its direction and hits a diffractive optical element DOE 16. The DOE 16 shapes the measuring laser beam 13 such that it intersects the optical axis 15 at a predetermined distance to the DOE 16. The DOE 16 is constructed such that the radial distance of the measuring laser beam 13 from the optical axis 15 determines the distance in which the measuring laser beam 13 intersects the optical axis 15. The greater the distance of the entry point of the measuring laser beam 13 from the optical axis 15, the greater is the distance of the DOE 16 from the intersection point of the exiting measuring laser beam 13 with the optical axis 15. It is thus possible to move the intersecting region between the measuring laser beam 13 and the optical axis 15 along the optical axis 15 by changing the radial position of the measuring laser beam 13 on the DOE 16.

As will be explained later, only the outer edge area of the DOE 16 has the function of shaping the measuring laser beam 13, while the inner or central area is reserved for other purposes.

It is intended that the detection of a layer boundary and/or the measurement of a layer thickness is performed not only in the optical axis 15 of the diagnostic device 1 but that it covers the entire surface. In particular, if the incident measuring laser beam 13 hits the vertex of a curved surface of a layer boundary, the measuring laser beam 13 is bounced back, in particular reflected, such that it is guided back, symmetrically to the incident measuring laser beam 13 with regard to the optical axis 15, via the beam path onto the scanning micromirror 12. Said scanning micromirror 12 reflects the bounced-back measuring laser beam 13 onto a detector 17 which may be designed, for example, as a ring-shaped large-area photodiode with amplifier circuit, said photodiode being preferably arranged concentrically to the optical axis 15. An evaluation unit 18 detects the back-reflected measuring laser beam 13 as a narrow pulse and can interpret said pulse as a detection state for a layer boundary. A similar narrow pulse is registered by the evaluation unit 18 as soon as another layer boundary in the eye 2 is analogously in a detection state. The layer thickness between the two detected layer boundaries can be deduced from a temporal correlation between the pulses and the position of the scanning micromirror 12 and from a knowledge of the beam path, in particular of the DOE 16.

A precise analytical solution for calculating the layer thickness is only possible after the topography measurement because the measuring laser beam 13 is refracted by the curved surfaces and the radii of curvature of the surfaces are initially unknown.

Figure 2:
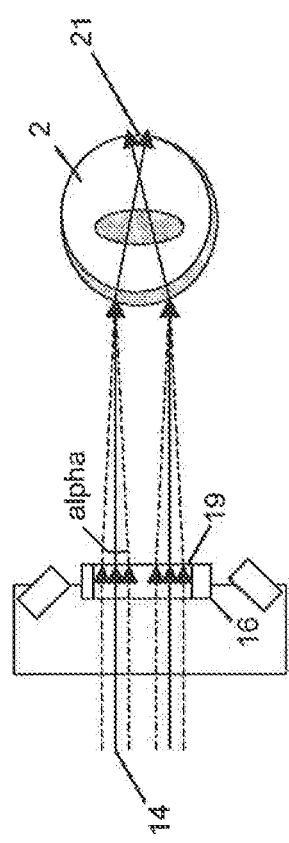
FIG. 2 a detail view of the accommodation beam path in FIG. 1.

FIG. 2 shows a very schematic view of the beam path of the accommodation laser beam 14. The accommodation laser beam 14 is deflected via the scanning micromirror 12 and passes through a central region of the DOE 16. A further DOE 19 or another optical element with comparable optical properties may be arranged in said central region of the DOE 16. An eye test character 21 is written directly and sharply focused on the retina of the eye 2 with the accommodation laser beam 14. So-called Landolt rings can be produced as eye test characters 21, for example.

To compensate for any refractive errors of the eye 2, the angle of incidence alpha of the accommodation laser beam 14 can be changed by using different radial regions of the DOE 19. The DOE 19 is designed such that the diffraction angle of the DOE 19 is a function of the distance to the optical axis 15. The aim is to produce an eye test character 21 on the retina of the eye 2 to be measured that is of the same size regardless of the refractive error of said eye. If the refractive error has a cylindrical shape, the eye test character 21 will be projected onto the eye 2 as an ellipse in the corresponding axis of the eye 2 to be measured so that the patient will see a circular ring. If the diagnostic device 1 is integrated into a wavefront measuring instrument, said wavefront measuring instrument can be used to measure and verify the image produced on the retina.

As an optional functionality, the existing measuring device can be used to determine the diopter range in which the eye 2 can still accommodate. The diopter range is the distance between the far point and the near point of focused vision. To take measurements of this range it is necessary to integrate the diagnostic device 1 into a wavefront measuring instrument.

With the scanning micromirror 12 of the lens 10 and the DOE 19, the eye test characters 21 are projected at different predefined angles alpha onto the eye 2. The eye 2 now tries to bend the intraocular lens 5 to create a sharply focused image of the eye test characters 21 on the retina. The adaptability of the refractive power of the eye can then be verified with the wavefront measuring instrument.

However, before the layer boundaries can be detected and, in particular, the layer thicknesses d1, d2 and/or d3 of the eye 2 can be measured, the eye 2 must be fixated. Preferably, the eye 2 will be measured in a relaxed state. To ensure that the eye 2 does not accommodate, a flashing dot or ring is projected as an eye test character 21 onto the retina with the scanning micromirror 12 and the patient is instructed to fixate on the eye test character 21. In this way the eye 2 is stabilized in a defined state.

It is, by the way, often the case that the accommodation laser beam 14 wanders across the eye 2 at different speeds so that the eye 2 does not perceive the brightness of the eye test character 21 as consistent. The light output of the laser diode module 7 can therefore be adapted, in particular modulated, depending on the location.

To allow for a coverage of the entire surface while detecting the layer boundaries and/or measuring the corneal thickness and/or the anterior chamber depth or other layer thicknesses, the eye test character 21 is moved on the retina in the X and Y direction perpendicular to the optical axis 15, whereby the patient is forced to turn or roll the eye 2. In this way the optical axis 15 intersects the eye 2 at different positions which can then be measured with regard to their layer thicknesses. This procedure ensures that each point of the eye 2 can be directly measured and thus a network of values measured for the layer thicknesses can be generated, which then forms the basis for the 3D model.

Another way of causing the eye to turn is to have the illuminating diodes 23, which are integrated in the eyepiece, flash selectively, thereby forcing the eye of the patient to turn by a predefined angle into all 4 directions.

In order to accurately record the detection state, the intersecting region between the measuring laser beam 13 and the optical axis 15 is not only moved along the optical axis 15 but also scanned laterally, e.g. in a linear or fan-shaped pattern, to safely adjust the detection state.

As shown in FIG. 1, an observation camera 22 and corresponding illuminating diodes 23 can be used to record the position of the eye 2, in particular the rotation angle. The result of the layer boundary detection or thickness measurement can thus be clearly identified. To ensure that the illuminating diodes 23 do not interfere with the measuring process, they are operated at a different wavelength so that the beams with their different wavelengths can be separated via filters, chromatic beam splitters etc.

Figure 3:
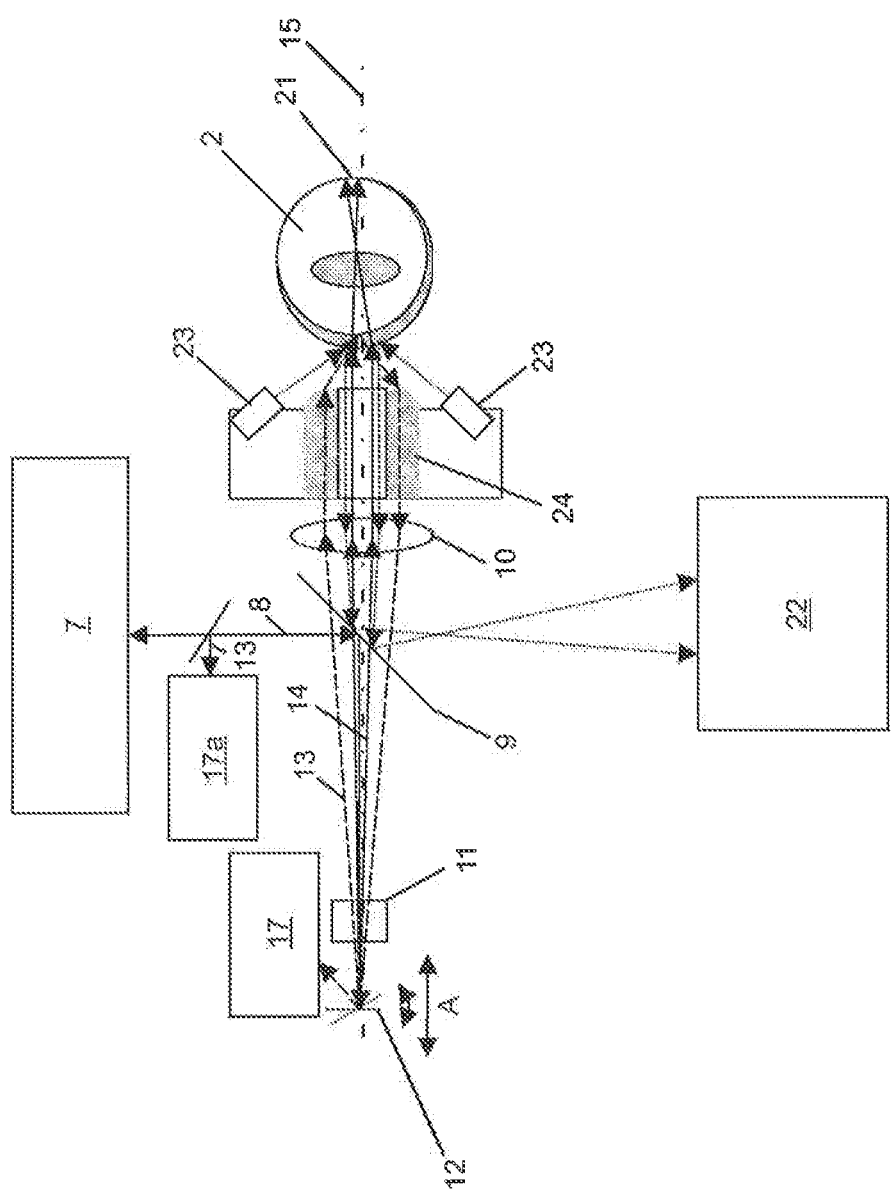
FIG. 3 a block diagram of a diagnostic device as a second embodiment of the invention.

A second embodiment of a diagnostic device 1 is depicted in FIG. 3, wherein the same reference symbols denote the same parts. Compared to the embodiment in FIG. 1, the position of the lens 10 has been moved so that it is now located on the side of the beam splitter 9 which faces away from the scanning micromirror 12. Furthermore, a sleeve element 24 replaces the DOE 16 that was located at the edge, said sleeve element 24 now having the task of shaping the measuring laser beams 13. Examples of such sleeve elements 24 will be described in the following. However, the sleeve element 24 is again designed such that a different deflection angle and/or a different deflection point is reached depending on the radial distance from the optical axis 15, so that the intersecting region between the measuring laser beam 13 and the optical axis 15 can be moved along the optical axis.

Figure 4:
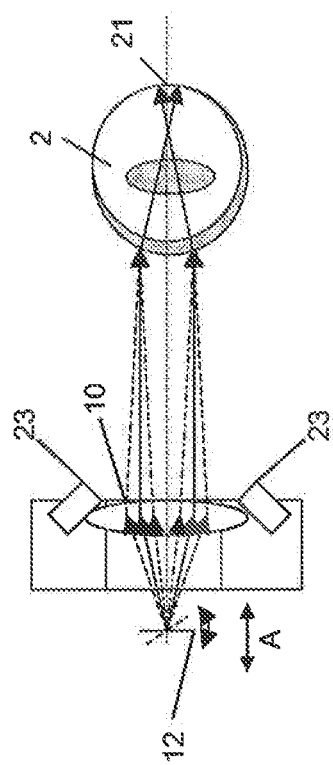
FIG. 4 a detail view of the accommodation beam path in FIG. 1.

The beam path of the accommodation laser beams 14 extends from the laser diode module 7 via the beam splitter 9 and the quarter-lambda waveplate 11 onto the scanning micromirror 12 which then guides the accommodation laser beam 14 through the beam splitter 9 and the lens 10, said lens 10 being designed either as a regular lens or as a gradient lens, and through the central open region of the sleeve element 24, as is shown in FIG. 4 as well. In the embodiment with a regular lens 10, refractive errors of the eye 2 are compensated for by a movement A of the scanning micromirror 12 along the optical axis 15, for example via a motorized carriage, in particular one with a piezo drive. Since the refractive error of the eye 2 must be compensated in this embodiment by adjusting the distance of the scanning micromirror 12 to the lens 10, the measuring laser beams 13 entering the sleeve element 24 will usually have an additional small angular component, depending on the refractive error of the eye to be measured. Such a small impact on the measuring area can be compensated for by adjusting the distance between the diagnostic device 1 and the eye 2 according to the refractive error of the eye 2.

FIG. 4 provides a very schematic view of the beam path of the accommodation laser beam 14 with the lens 10 being a gradient lens. The accommodation laser beam 14 is deflected via the scanning micromirror 12 and passes through a central region of the lens 10. An eye test character 21 is written directly and sharply focused on the retina of the eye 2 with the accommodation laser beam 14.

To compensate for any refractive errors of the eye 2, the angle of incidence alpha of the accommodation laser beam 14 can be changed by using different radial regions of the lens 10. The lens 10 is designed such that the exit angle of the lens 10 is a function of the distance to the optical axis 15. The aim is to produce an eye test character 21 on the retina of the eye 2 to be measured that is of the same size regardless of the refractive error of said eye.

In this embodiment, the measuring laser beam 13—once it hits the vertex of a curved surface of a layer boundary in the optical axis 15—is again reflected such that it is coupled into the sleeve element 24 at the side of the sleeve element 24 that is facing away in FIG. 3, in particular mirror-symmetrically to the optical axis 15. The beam path is designed such that, in the detection state, the measuring laser beam 13 reflected at the boundary layer is bounced back onto the scanning micromirror 12. Said scanning micromirror 12 guides the beam onto the detector 17 which is designed, arranged and/or connected analogously to the detector 17 in FIG. 1.

Figure 5:
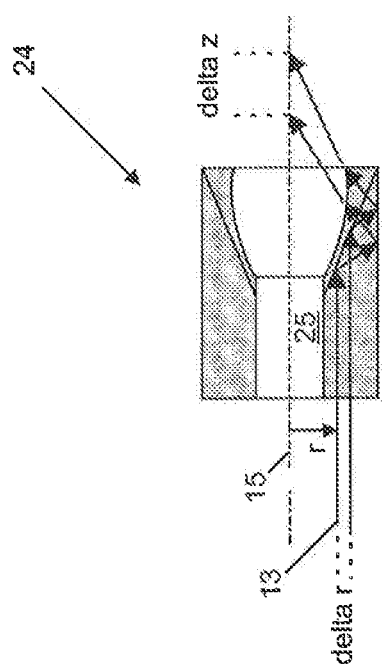
FIG. 5-9 embodiments of an optical ring element for use in the diagnostic device of FIG. 1 or FIG. 3.
Figure 6:
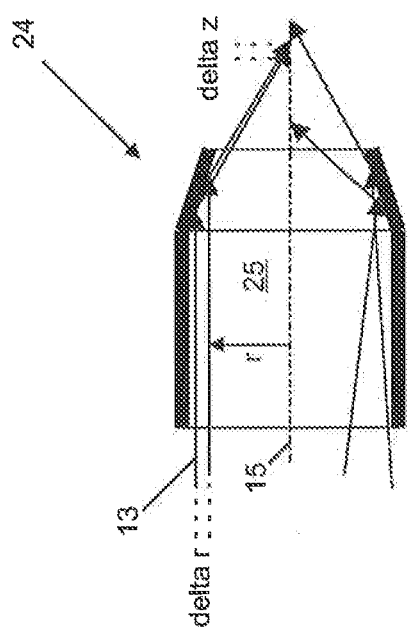

FIGS. 5 and 6 each show a sleeve element 24 which can be inserted into the embodiment of FIG. 3 or can replace the DOE 16 in FIG. 1. The sleeve element 24 has a free aperture 25 and is designed such that the direction and/or position of a reflected measuring laser beam 13 depends on the radial distance r from the optical axis 15 of the incident measuring laser beam 13.

The embodiment shown in FIG. 5 is a reflective element, wherein a funnel-shaped section with a reflecting inner surface is arranged at the exit side. If the incident measuring laser beam 13 has an offset delta r of the radial position, the funnel-shaped section provides the reflected measuring laser beam 13 with an offset delta z in the direction of the optical axis 15. Of course it is also possible to use a curved funnel shape instead of a simple straight one to further spread the offset delta z.

FIG. 6, on the other hand, shows a sleeve element 24 where the measuring laser beam 13 propagates in the material of the sleeve element 24. This sleeve element 24 again has a funnel-shaped section, but here the measuring laser beam 13 is guided into the material of the funnel-shaped section for the purpose of shaping and/or guiding the beam. With this sleeve element 24, as well, a depth offset delta z along the optical axis 15 results from a radial offset delta r.

Figure 8:
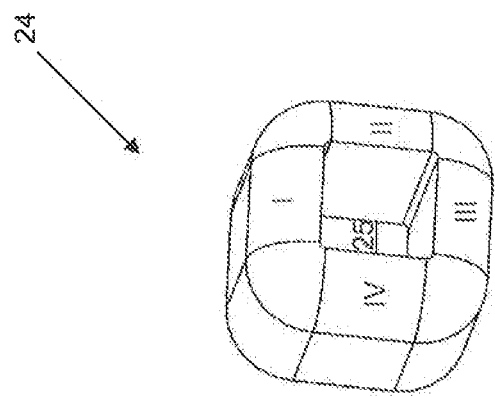
Figure 7:
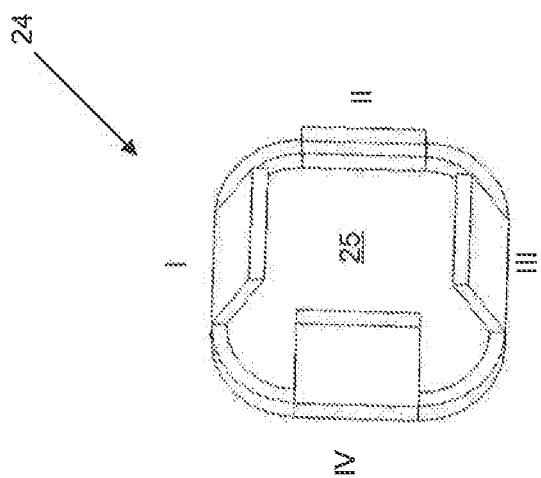

FIGS. 7 and 8 show two further embodiments of the sleeve element 24 in a schematic three-dimensional view. The sleeve element 24 in FIG. 7 is designed as a reflective optical element with mirror surfaces, while the one in FIG. 8 is designed as a refractive optical element. Both sleeve elements 24 have different regions I, II, III, IV in the direction of rotation, with pairs of said regions facing each other. For example, the regions I-III and the regions II-IV face each other. When detecting the layer boundary, in particular in the detection state, the measuring laser beam is guided via one region of a pair to the eye 2 and guided back via the other region of the same pair. In particular, the regions allow for scanning the eye 2 in lateral directions and in the depth direction, thus making it possible to scan a volume by moving the measuring laser beam 13.

The other pair can be designed for the same depth region of the eye and can thus perform the same measurement as the first pair, only offset by 90° around the optical axis. This embodiment improves the measurement reliability of the diagnostic device 1. In other embodiments, the regions of the two pairs I-III and II-IV have different angles of inclination so that these pairs can scan different regions in the eye. For example, the pair I-III may be designed for measuring the corneal thickness d1 and the pair II-IV for measuring the intraocular lens thickness d3. The refractive regions of the sleeve element in FIG. 8 may be pairs adjusted to each other in the same way.

Figure 9:
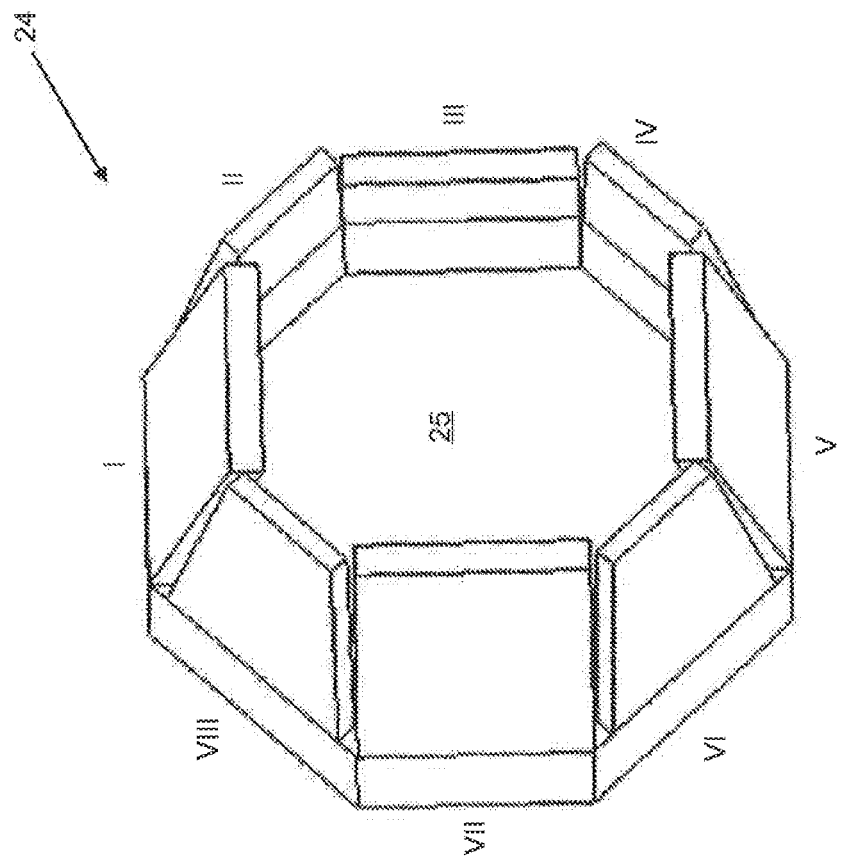

FIG. 9 shows a further embodiment of a sleeve element which has eight regions I-VIII. The regions are assigned as follows:

I-V: corneal thickness, horizontally
III-IV: corneal thickness, vertically
II-IV: intraocular lens thickness in a first direction
IV-VIII: intraocular lens thickness perpendicular to the first direction.

Figure 10:
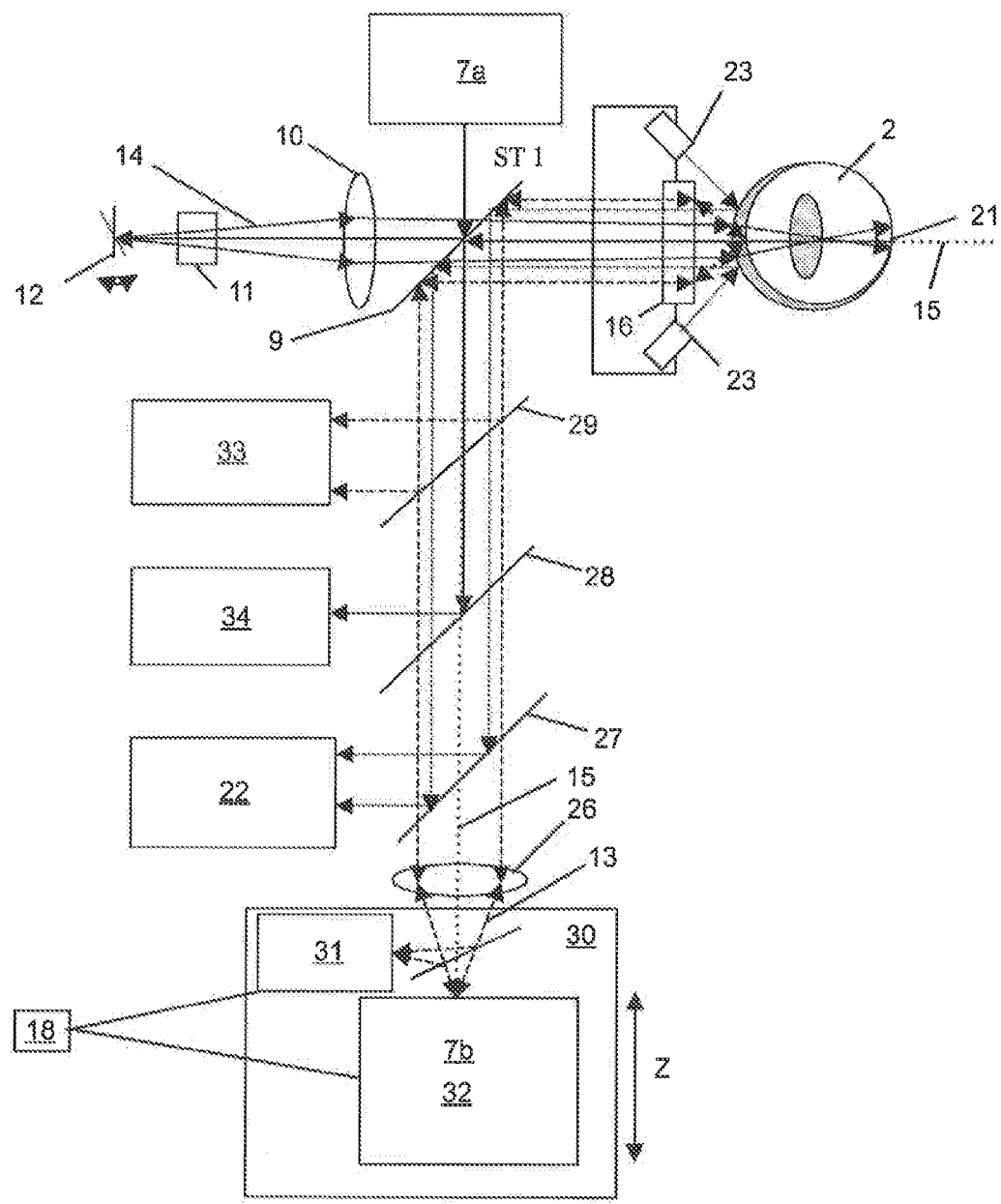
FIG. 10 a block diagram of a diagnostic device as a third embodiment of the invention.

FIG. 10 shows a third embodiment of the invention which is different from the embodiments in FIGS. 1 and 3 insofar as the accommodation laser beams 14 and the measuring laser beams 13 are generated by different laser diode modules 7a and 7b, respectively.

With regard to a description of the accommodation beam path we refer to the description of the first embodiment in FIG. 1 and to the explanations regarding FIG. 2, respectively.

The measuring laser beam path, on the other hand, has a different design here. In this embodiment, a laser diode module 7b generates a measuring laser beam 13 which is divergent at first, is then collimated via a collimating lens 26 and guided, in its expanded state, through a multitude of beam splitters 27, 28 and 29. The collimated measuring laser beam 13 then hits the beam splitter 9 which focuses said measuring laser beam from the DOE 16 onto the optical axis 15 at a specified distance to the DOE 16. Here, as well, a lens can be used instead of the DOE 16.

The laser diode module 7b is mounted on a carriage 30 which is slidable in a Z direction, with the Z direction corresponding to the optical axis 15 tilted by the beam splitter 9. By moving the laser diode module 7b, the focal position or the image plane of the measuring laser beam 13 in the eye 2 changes. If the focus or the image of the laser source of the laser diode module 7b falls on a boundary layer in the eye 2 and is on a vertex at the same time, the measuring laser beam 13 is reflected back on an identical path and is bounced back either into a detector 31 on the carriage 28 or onto a detector 32 which is integrated in the laser diode module 7b. The evaluation unit 18 is connected to the detector 31 or 32 such that this state can be recognized as the detection state. The measurement technique is therefore the same as the measurement technique of confocal microscopy.

In analogy to the previously described embodiments, the layer thickness between the layer boundaries is determined by comparing the position of the actuator, meaning the carriage 30, in detection states of different layer boundaries.

As an optional functionality, the diagnostic device 1 can have a topography measuring unit 33, e.g. a Shack-Hartmann sensor, for measuring the curvature or the curvature characteristics of the cornea, and/or a wavefront measuring unit 34 for measuring the local refractive power or the local ametropia of the eye 2.

In a first alternative method of measuring the layer thickness, a second optical axis 35, which does not overlap with the optical axis 15 of the diagnostic device, is selected as the optical axis in the eye 2.

Figure 12:
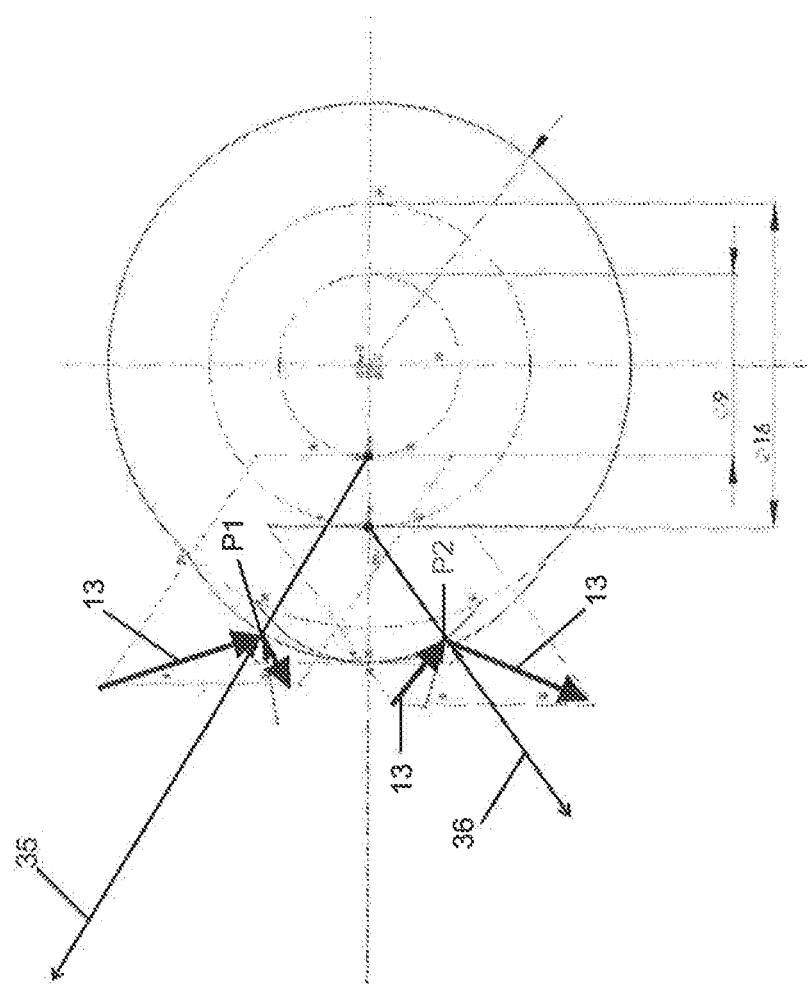
FIG. 12 another schematic cross-sectional view of a human eye with measuring laser beams in a detection state.

In a first alternative sketched in FIG. 12, the measuring laser beam 13 hits the external side of the cornea 3 at a point P1 which is located outside the optical axis 15 of the diagnostic device. Instead, the point P is located on a second optical axis 35 which intersects the center of curvature of the external side of the cornea 3. The measuring laser beam 13 reflected in the point P1 is bounced back again in the direction of the diagnostic device and hits the detector 17, thus ensuring that this state is recognized as a detection state.

In this detection state, the beam is shaped by making an adjustment to the DOE 16. For example, the DOE 16 may have a square or hexagonal shape, as shown in FIGS. 7 to 9, instead of having a circular shape, as shown in FIG. 5 or 6. For example, the sides can be arranged in pairs such that the individual measuring laser beams 13 are shaped such that they scan the thicknesses and relative distances of the curved surfaces in the eye 2 in a sectional plane that is parallel to the respective side of the DOE 16. By moving the scanning micromirror 12, the DOE 16 generates a bundle of rays on each side which intersects the eye 2 in its depth in a fan-shaped pattern. The sectional plane may be, for example, perpendicular or at an angle to the sheet plane in FIG. 12. The bundle of rays does not necessarily have to be parallel to the sides of the DOE 16. Thus, one, two, four or more narrow slits, the number depending on the embodiment, each having a length of 8 to 10 mm, are projected onto the eye 2 and intersect the eye 2.

In the square embodiment according to FIGS. 7 and 8, the measurement of the eye 2 is performed with two vertical lines, while in the hexagonal embodiment 4 lines arranged at angles of 45 degrees are used. The detector 17 is hit exclusively by the beam reflected by a boundary layer, said beam being located, together with the incident beam, in the measurement plane which intersects the center of curvature on the cornea and lies on the second optical axis 35. In the measurement plane, the incident measuring laser beam 13 and the reflected measuring laser beam 13 have to extend perpendicular or at an angle to the sectional plane and intersect the eye 2. The detector 17 can only receive the measuring laser beams 13 which, as shown in FIG. 12, leave the diagnostic device 1 as incident beams from the top right of the Figure and enter the diagnostic device 1 as measuring laser beams 13 reflected by the eye 2 at the bottom right of the Figure. Given the time of the reflection reported by the detector 17, it is possible to clearly identify the position and the angle of the measuring laser beam 13 entering the eye 2. It can be seen in the bottom part of FIG. 12 that a second boundary layer can be detected analogously, with the point of reflection P2 now being located on a third optical axis 36 which intersects the center of curvature of that boundary layer.

If several points P of a boundary layer are detected, in particular if said points are located adjacent to the intersection point of said boundary layer with the optical axis 15, a radius of curvature of the boundary layer in the measurement plane can be determined. This modification thus adds a "topography measurement" function to the diagnostic device 1. The DOE 16 can be optimized depending on the various requirements in terms of measurement range, measurement accuracy and variables to be measured, such as corneal thickness, anterior chamber depth and intraocular lens thickness. The layer from which the reflection originates can be determined through the intensity of the reflected measuring beam.

The reference point for the topography measurement is the intersection point of the cornea 2 with the optical axis 15. This point can be determined very accurately with the measurement technique. The curvature of the cornea 2 in the respective sectional plane or measurement plane of the eye 2 can be determined with three and more measuring points. If the x and y coordinates of at least three measuring points are known, the radius of curvature and the center of curvature of the cornea 2 can be calculated.

Figure 13:
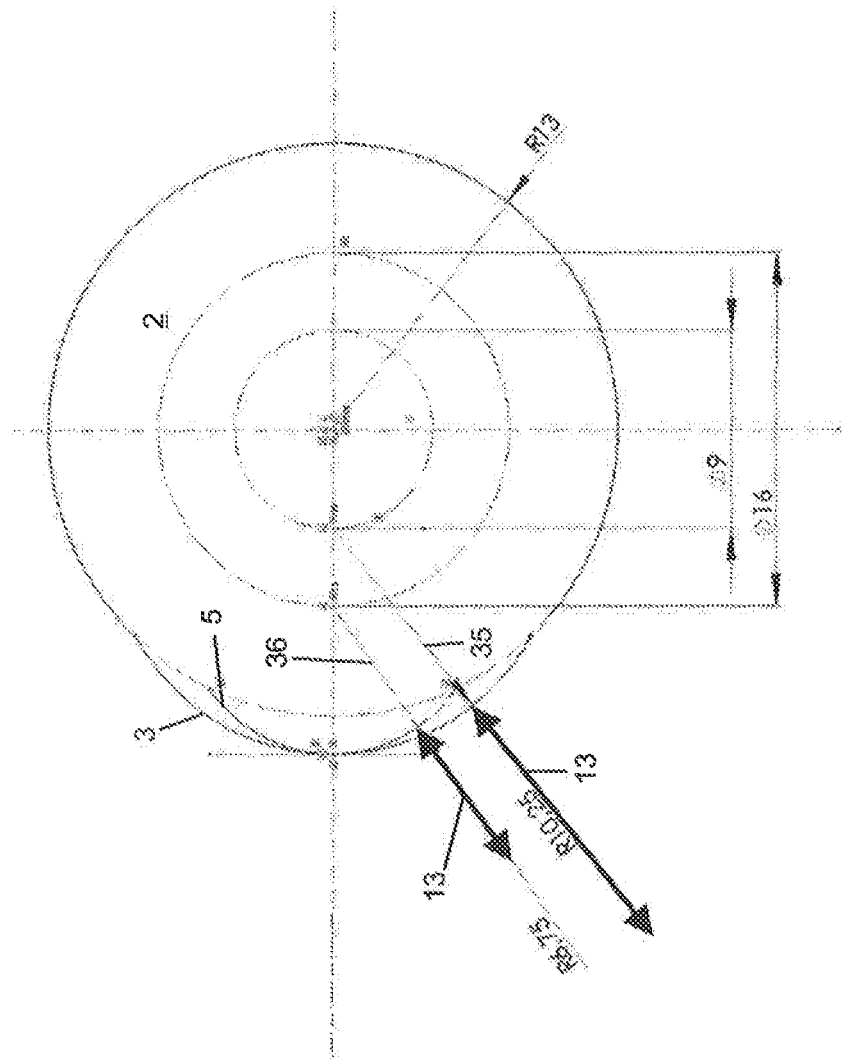
FIG. 13 another schematic cross-sectional view of a human eye with other measuring laser beams in a detection state.

In another embodiment according to FIG. 13, the topography measurement and the layer thickness measurement are carried out by reflecting the measuring laser beams 13 into themselves. Instead of the detector 17, another detector with identical functionality may be arranged at a different location in this embodiment. For example, a detector can be integrated in the laser diode module 7 or a detector 17a can be arranged in front of the laser diode module 7, said detector being able to receive the reflected measuring laser beam 13 via a beam splitter 9a. The detectors 17, 17a etc. can be designed as a photodiode or a position detector or a CCD chip or as a photodiode integrated in the laser diode module.

The angles of the measuring laser beams 13 must be shaped by the diffractive optical element DOE 16 for this measurement technique. The DOE 16 (or a lens as a gradient lens) generates e.g. a parallel fan of rays in the sectional plane, said rays intersecting the optical axis 36 at different points. Only a measuring laser beam 13 that hits the boundary layer perpendicular to the curved surface will be reflected into itself. The reflected measuring laser beam 13 reaches the detector 17a or the detector in the laser diode module 7 via the scanning micromirror 12 which also serves as an aperture (FIG. 1). The measurement accuracy can be increased by recording the exact position and intensity of the reflected beam with the detector 17a. The layer which has caused the reflection can be determined through the intensity of the reflected measuring beam.

The easiest way to reflect the measuring laser beams 13 into themselves would be an ideal lens which creates a focal point in the center of curvature of the cornea or an equivalent embodiment of the DOE 16. The disadvantage of this measurement technique is that the position of the vertex must be known to determine the radius of curvature. This is due to the fact that concentric spheres with different radii provide the same back reflection.

The number of measuring points can be increased by extending the angular range generated by the device. The same can be achieved by changing the distance of the scanning micromirror 12 to the lens 10. In this way the curvature of the cornea can be measured covering the entire surface without the need for turning the eye 2.

1 diagnostic device
2 eye
3 cornea
4 anterior chamber
5 lens
6 vitreous body
7a, b laser diode module
8 laser beam
9 beam splitter
10 lens
11 quarter-lambda waveplate
12 scanning micromirror
13 measuring laser beam
14 accommodating laser beam
15 optical axis
16 DOE
17 detector
18 evaluation unit
19 DOE
20 lens
21 eye test character
22 observation camera
23 illuminating diodes
24 sleeve element
25 aperture
26 collimating lens
27 beam splitter
28 beam splitter
29 beam splitter
30 carriage
31 detector
32 detector
33 topography measuring unit
34 wavefront measuring unit

The invention claimed is:

1. A diagnostic device for detecting a layer boundary in an eye, comprising:
 a light source, wherein the light source defines an object plane,
 a sensor unit,
 a beam path which is designed to guide at least one measuring beam of the light source from the object plane of the light source into an intersecting region of the measuring beam with an optical axis in the eye,
 an actuator comprising a 2D scanning mirror designed to move the intersecting region along the optical axis,
 the beam path is designed such that, in a detection state, the measuring beam is guided from a layer boundary as a bounced-back measuring beam into the sensor unit if the intersecting region is located on the layer boundary and, in the detection state, the measuring beam is guided back to the center unit on a different beam path at least between the eye and a last optical element, and
 an evaluation unit which is designed to recognize the detection state on the basis of the signals of the sensor unit,
 the evaluation unit is designed to estimate and/or determine a layer thickness between a first and a second layer boundary on the basis of the position of the actuator in a detection state of the first and the second layer boundary,
 the measuring beam being guided as an unexpanded, single measuring beam through the beam path, wherein the measuring beam has a diameter (FWHM) that is always less than 2 mm between the last optical element and the eye, and the actuator moves a lateral position of the measuring beam in the eye to move the intersecting region along the optical axis,
 wherein the measuring beam scans the eye in the depth direction along the optical axis by way of the 2D scanning mirror and the bounced-back measuring beam scans laterally to reach the detection state by way of the 2D scanning mirror, the 2D scanning mirror reflecting the bounced-back measuring beam onto the sensor unit in the detection state, and
 wherein the last optical element that guides the measuring beam onto the intersecting region is designed as one of a diffractive optical element, a diffractive element, a reflection element, and a refractive element, and
 the last optical element is a ring element having a plurality of regions in the direction of rotation, pairs of said regions being assigned to a layer boundary in the eye such that, in the detection state, the measuring laser beam is guided by one region of one of the pairs of said regions to the eye and guided back via the other region of the one of the pairs of said regions, and the beam path is designed to send accommodation beams through a central opening of the ring element for forming an accommodation target.

2. The diagnostic device of claim 1, wherein
 a spatial filter and/or an aperture is arranged in the beam path in front of the sensor unit, and/or
 the sensor unit is a unit with spatial resolution.

3. The diagnostic device of claim 1, wherein
 the beam path is designed such that the measuring beam for detecting the layer boundary is restricted to one ring area or a smaller area which leaves a central region on the last optical element uncovered.

4. The diagnostic device of claim 1, wherein
 the light source or a further light source is designed to create the accommodation target.

5. The diagnostic device of claim 1 wherein
 an accommodation target can be formed which appears to the eye to be coming from different directions.

* * * * *